US008168619B1

(12) United States Patent
Paris et al.

(10) Patent No.: US 8,168,619 B1
(45) Date of Patent: May 1, 2012

(54) HORMONAL COMPOSITION BASED ON A PROGESTATIONAL AGENT AND AN OESTROGEN AND USE THEREOF

(75) Inventors: Jacques Paris, Nice (FR); Jean-Louis Thomas, Charenton-le-Pont (FR)

(73) Assignee: Laboratoire Theramex (MC)

( * ) Notice: Subject to any disclaimer, the term of this patent is extended or adjusted under 35 U.S.C. 154(b) by 0 days.

(21) Appl. No.: 09/423,109

(22) Filed: Oct. 29, 1999

(30) Foreign Application Priority Data

Oct. 25, 1999 (WO) .................. PCT/FR99/02588

(51) Int. Cl.
*A61K 31/56* (2006.01)
*A61K 9/00* (2006.01)
*A61K 9/14* (2006.01)

(52) U.S. Cl. ......... 514/170; 514/178; 514/182; 424/484

(58) Field of Classification Search .................. 514/170, 514/169, 182, 179, 171, 178; 424/484
See application file for complete search history.

(56) References Cited

U.S. PATENT DOCUMENTS

| | | | |
|---|---|---|---|
| 4,820,831 A | 4/1989 | Ogata et al. | |
| 4,826,831 A | 5/1989 | Plunkett | |
| 5,108,995 A | 4/1992 | Casper | |
| 5,208,225 A | 5/1993 | Boissoneault et al. | |
| 5,256,421 A | 10/1993 | Casper | |
| 5,382,573 A | 1/1995 | Casper | |
| 5,552,394 A | 9/1996 | Hodgen | |
| 5,565,443 A | 10/1996 | Lanquetin et al. | |
| 5,585,370 A | 12/1996 | Casper | |
| 5,843,934 A | 12/1998 | Simpkins | |
| 5,888,543 A | 3/1999 | Gast | |
| 5,891,867 A | 4/1999 | Lanquetin et al. | |
| RE36,247 E * | 7/1999 | Plukett et al. ................. | 514/170 |
| 6,500,814 B1 | 12/2002 | Hesch | |
| 6,831,073 B1 | 12/2004 | Lanquetin et al. | |
| 6,906,049 B1 | 6/2005 | Paris et al. | |
| 7,030,104 B2 * | 4/2006 | Gray et al. ..................... | 514/170 |
| 7,749,987 B2 | 7/2010 | Paris et al. | |
| 8,071,576 B2 * | 12/2011 | Coelingh Bennink et al. ............................ | 514/170 |
| 2004/0220163 A1 | 11/2004 | Paris et al. | |
| 2007/0281912 A1 | 12/2007 | Paris | |
| 2008/0242650 A1 | 10/2008 | Thomas | |

FOREIGN PATENT DOCUMENTS

| | | |
|---|---|---|
| EP | 0136011 | 4/1985 |
| EP | 0 235 090 A1 | 9/1987 |
| EP | 0 309 263 | 9/1987 |
| EP | 0 309 263 A1 | 3/1989 |
| EP | 0 491 415 A1 | 6/1992 |
| EP | 0 136 011 B1 | 1/1997 |
| EP | 0 235 607 A1 | 1/1998 |
| EP | 1 227 814 B1 | 1/2005 |
| FR | 2737411 | 2/1997 |
| FR | 2754179 | 4/1998 |
| GB | 2 216 420 | 10/1989 |
| WO | WO 96/09826 | 4/1996 |
| WO | WO 96/10991 | 4/1996 |
| WO | WO 97/04787 | 2/1997 |
| WO | WO 98/15279 | 4/1998 |
| WO | WO 01/30355 A1 | 5/2001 |
| WO | WO 01/30358 A1 | 5/2001 |

OTHER PUBLICATIONS

Blanc et al. (Clinical Therapeutics, 1998), 20(5), 901-912).*
U.S. Appl. No. 11/649,672, filed Jan. 3, 2007.
French Patent No. 2754179 A1, issued Apr. 10, 1998.
Canadian Patent No. 1332227, issued Oct. 4, 1994.
Cano, et al., (1991). "Effect of Continuous Oestradiolmedroxyprogesterone Administration on Plasma Lipids and Lipoproteins," Maturitas, 13(1):35-42.
Catherino, et al., (1995). "Nomegesterol Acetate, a Clinically Useful 19-Norprogesterone Derivative Which Lacks Estrogenic . . . ," J. Steriod Biochem. Mol. Biol., 55(2):239-46.
Fraser, et al., (1991). "The Effects of the Additional of Nomegestrol Acetate to Post-Menopausal Oestrogen Therapy," Maturitas, 11(1):21-34.
Jamin, (1992). "Female Contraception by a Normal Dose Progestogen After 40 Years of Age. Possible Association . . . ," Rev. Fr. Gynecol. Obstet., 87(6):370-376, English Abstract.
Sitruk-Ware, (1995). "Pharmacology of Oral Contraceptives," Rev. Prat., 45 (19):2401-2406, English Abstract.
Affinito et al., (1998). Ultrasonographic measurement of endometrial thickness during hormonal replacement therapy in postmenopausal . . . Ultrasound Obstet Gynecol, 11:343-346.
Basdevant et al., (1991). Effects of Nomegestrol Acetate (5mg/d) On Hormonal, Metabolic and Hemostatic Parameters in Premenopausal Woman. Contraception, 44(6):599-605.
Bernard A.M. et al., (1994). Menopausal: Bone and Therapeutic Regimens (Cont). International Journal of Gynecology & Obstetrics, pp. 124.
Birkauser M. et al. (1995). Substitution Hormonale: Une Indication Bien Posee et Des Schemas, De Traitement Individuels Sont Determinants . . . Med et Hyg, 53:1770-3.
Bocanera R. et al., (1993). Effect of a HRT Regime (micronized 17—estradiol and medroxy progesterone acetate) On The . . . Bleeding and Endometrial Function, p. 17, Abstract 40.
Carranza-Lira, (1998). Endomerial Changes According to Hormone Replacement Therapy . . . Menopause: The Journal of The North American Menopause Society, 5(2):86-89.
Doren et al., (1996). Long-term Compliance of Continuous Combined Estrogen and Progestogen . . . Journal of the Climacteric & Postmenopause, 25:99-105.
Doren et al., (1997). Uterine Perfusion and Endometrial Thickness in Postmenopausal Women on Long-term . . . Ultrasound Obstet. Gynecol., 9:113-119.

(Continued)

Primary Examiner — Sabiha Qazi
(74) Attorney, Agent, or Firm — John P. White; Cooper & Dunham LLP

(57) ABSTRACT

A method of preventing estrogen deficiencies and osteoporosis in menopausal women by continuously orally administering without interruption to menopausal women in need thereof an amount of 0.3 to 3 mg of 17β-estradiol or esters thereof and 0.3 to 1.25 mg of nomegestrol or esters thereof in an amount sufficient to prevent said problems.

5 Claims, No Drawings

OTHER PUBLICATIONS

Doren & Scheider, (1996). The Impacts of Different HRT Regimens on Compliance. Int. J. Fertil., 41(1):29-39.

Drapier Faure E. (1992). Le Traitement de la Menopause Evitant Les Regles: Est-il Possible? Est-il . . . Gynecologie, 43(4-5):271-280, including English Summary at p. 271.

Eiken et al., (1996). Effects of 10 Years' Hormone Replacement Therapy on Bone Mineral Content in Postmenopausal Women. Bone, 19(5):191S-193S.

Eiken et al., (1997). Effect on Bone Mass After Eight Years of Hormonal Replacement Therapy. British Journal of Obstetrics and Gynaecology, 104:702-707.

Eiken and Kolthoff, (1995). Compliance With Long-Term Oral Hormonal Replacement Therapy. Maturitas, 22:97-103.

Ettinger et al., (1998). Comparison of Continuation of Postmenopausal Hormone Replacement . . . Menopause: The Journal of The North American Menopause Society, 5(3):152-156.

Fox H. et al., (1993). Six months Endometrial Histology data on Continuous Estradiol combined . . . Bleeding and Endometrial Function, p. 40, Abstract 119.

Hargrove J.T. et al., (1989). Menopausal Hormone Replacement Therapy With Continuous Daily Oral Micronized Estradiol and Progesterone. Obstetrics & Gynecology, 73:606-612.

Hart et al., (1998). Long-Term Effects of Continuous Combined HRT on Bone Turnover and Lipid Metabolism in Postmenopausal Women. Osteoporosis Int., 8:326-332.

Kuhl, (1996). Comparative Pharmacology of Newer Progestogens. Drugs, 51(2):188-215.

Muzanuma et al., (1997). Prevention of Postmenopausal Bone Loss With Minimal Uterine Bleeding Using . . . Maturitas, 27:69-76.

Neumann, (1977). Probleme der Dosisfindung:Sexualhormone. Drug Res., pp. 296-318, including English Summary at p. 296.

Oettel et al., (1999). The Preclinical and Clinical Profile of Dienogest: A Short Overview. Drugs of Today, 35:3-12.

Paterson et al., (1980). Endometrial disease after treatment with oestergens and progestogens in the climacteric. British Medical Journal, pp. 822-824.

Piegsa et al., (1997). Endometrial status in post-menopausal woman on long-term continuous combined hormone . . . European Journal of Obstetrics & Gynecology, 72:175-180.

Rauch and Taubert. (1993). Continuous hormone replacement therapy with estradiol valerate and chlormadinone acetate in adjectable dosages. Maturitas, 17:123-127.

Recker et al., (1999). The Effect of Low-Dose Continuous Estrogen and Progesterine Therapy with Calcium and Vitamin D Bone in Elderly Women. Ann Intern Med., 130:897-904.

Reubinoff et al., (1995). Effects of hormone replacement therapy on weight, body, composition, . . . Fertility and Sterility, 64(5):963-968.

Stadberg et al., (1996). 17B-estradiol and norethisterone acetate in low doses as continuous combined hormone replacement therapy. Maturitas, 23:31-39.

Thomas et al., (1993). Postmenopausal Hormone Therapy. 7th Intern. Cong. on the Menopause, Stockholm, Abstract No. 372.

Ulrich et al., (1997). Quality of life and patient preference for sequential versus continuous . . . International Journal of Gynecology & Obstetrics, 59:S11-S17.

Whitehead et al., (1982). Effects of Various Types and Dosages of Progestogens on the Postmenopausal Endometrium. The Journal of Reproductive Medicine, 27(8):539-548.

Wolfe and Huff, (1995). Effects on Continuous Low-Dosage Hormonal Replacement Therapy on Lipoprotein Metabolism in Postmenopausal Women. Metabolism, 44(3):410-417.

Wolfe and Plunkett, (1994). Early effects of continuous Low-Dosage dl-norgestrel administered alone or with estrogen. Maturitas, 18:207-219.

Affinito et al., (1998) "Ultrasonographic Measurement of Endometrial Thickness During Hormonal Replacement Therapy in Postmenopausal Women" Ultrasound Obstet. Gynecol, 11:343-346.

Basdevant et al., (1991) "Effects of Nomegestrol Acetate (5 mg/D) on Hormonal, Metabolic and Hemostatic Parameters in Premenopausal Women" Contraception, 44 (6) : 599-605.

Bernard A. M. et al., (1994) "Menopausal: Bone and Therapeutic Regimens (Cont)." International Journal of Gynecology & Obstetrics, pp. 124.

Birkauser M. et al., (1995) "Substitution Hormonale: Une Indication Bien Posee et Des Schemas De Traitement Individuels Sont Déterminants Pour Le Succes Du Traitement" Med. et Hyg., 53:1770-3.

Bocanera R et al., (1993). "Effect of a HRT Regime (Micronized 17-Estradiol and Medroxy Progesterone Acetate) On The Endometria and Bleeding Pattern of Climacteric Women" Bleeding and Endometrial Function, p. 17, Abstract No. 40.

Carranza-Lira, (1998). "Endometrial Changes According to Hormone Replacement Therapy Schedule" Menopause: The Journal of The North American Menopause Society, 5(2):86-89.

Doren et al., (1996). "Long-Term Compliance of Continuous Combined Estrogen and Progestogen Replacement in Postmenopausal Women." Journal of the Climacteric & Postmenopause, 25:99-105.

Doren et al., "Uterine Perfusion and Endometrial Thickness in Postmenopausal Women on Long-Term Continuous Combined Estrogen and Progestogen Replacement" Ultrasound Obstet. Gynecol., 9:113-119.

Doren & Scheider, (1996). "The Impacts of Different HRT Regimens on Compliance" Int. J. Fertil., 41(1) :29-39.

Drapier Faure E.. (1992). "Le Traitement De La Menopause Evitant Les Regles: Est-il Possible? Est-Il Souhaitable?" Gynecologie, 43(4-5):271-280, Including English Summary At p. 271.

Eiken et al. (1996) "Effects of 10 Years' Hormone Replacement Therapy on Bone Mineral Content in Postmenopausal Women" Bone, 19(5):191S-193S.

Eiken et al. (1997). "Effect on Bone Mass After Eight Years of Hormonal Replacement Therapy" British Journal of Obstetrics and Gynecology 104:702-707.

Eiken and Kolthoff, (1995). "Compliance With Long-Term Oral Hormonal Replacement Therapy" Maturitas 22:97-103.

Ettinger et al.,(1998)."Comparison of Continuation of Postmenopausal Hormone Replacement Therapy: Transdermal Versus Oral Estrogen" Menopause: The Journal of the North American Menopause Society, 5(3):152-156.

Fox H. et al, (1993)"Six Months Endometrial Histology Data on Continuous Estradiol Combined With 4 Different Dosages of Continuous Dydrogesterone in more than 300 Postmenopausal Women" Bleeding and Endometrial Function, p. 40, Abstract 119.

Hargrove J.T. et al.,(1998) "Menopausal Hormone Replacement Therapy With Continuous Daily Oral Micronized Estradiol and Progesterone", Obstetrics & Gynecology, 73:606-612.

Hart et al.,(1998) "Long-Term Effects of Continuous Combined HRT on Bone Turnover and Lipid Metabolism in Postmenopausal Women" Osteoporosis Int., 1998, 8:326-332.

Kuhl (1996). "Comparative Pharmacology of Newer Progestogens" Drugs, 51(2):188-215.

Mizanuma et al., (1997). "Prevention of Postmenopausal Bone Loss With Minimal Uterine Bleeding Using Low Dose Continuous Estrogen/Progestin Therapy: A 2 Year Prospective Study" Maturitas 27:69-76.

Neumann, (1977)."Probleme der Dosisfindung:Sexualhormone" Drug. Res., pp. 296-318, Including English Summary at p. 296.

Oettel et al., (1999). "The Preclinical and Clinical Profile of Dienogest: A Short Overview", Drugs of Today,35:3-12.

Paterson et al., (1980)."Endometrial Disease After Treatment With Oestrogens and Progestogens in the Climacteric" British Medical Journal, pp. 822-824.

Piegsa et al., (1997)."Endometrial Status in Post-Menopausal Women on Long-Term Continuous Combined Hormone Replacement Therapy (Kliofem) A Comparative Study of Endometrial Biopsy, Outpatient Hysteroscopy and Transvaginal Ultrasound" European Journal of Obstetrics & Gynecology, 72:175-180.

Rauch and Taubert, (1993)."Continuous Hormone Replacement Therapy With Estradiol Valerate and Chlormadinone Acetate in Adjustable Dosages" Maturitas, 17:123-127.

Recker et al.,(1999). "The Effect of Low-Dose Continuous Estrogen and Progesterone Therapy With Calcium and Vitamin D Bone in Elderly Women" Ann Internal Med., 130:897-904.

Reubinoff et al., (1995). "Effects of Hormone Replacement Therapy on Weight, Body, Composition, Fat Distribution, and Food Intake in Early Postmenopausal Women: A Prospective Study" Fertility and Sterility, 64 (5) : 963-968.

Stadberg et al., (1996)."17B-Estradiol and Norethisterone Acetate in Low Doses As Continuous Combined Hormone Replacement Therapy" Maturitas, 23:31-39.

Thomas et al., (1993)."Postmenopausal Hormone Therapy" 7th Intern. Cong. on the Menopause, Stockholm, Abstract No. 372.

Ulrich et al., (1997). "Quality of Life and Patient Preference for Sequential Versus Continuous Combined HRT: The UK Kliofem Multicenter Study Experience" International Journal of Gynecology & Obstetrics, 59:S11-S17.

Whitehead et al., (1982)."Effects of Various Types and Dosages of Progestogens on the Postmenopausal Endometrium" The Journal of Reproductive Medicine, 27(8):539-548.

Wolfe and Huff, (1995)."Effects of Continuous Low-Dosage Hormonal Replacement Therapy on Lipoprotein Metabolism in Postmenopausal Women" Metabolism, 44(3):410-417.

Wolfe and Plunkett, (1994). "Early Effects of Continuous Low- Dosage D1-Norgestrel Administered Alone or With Estrogen" Maturitas,18:207-219.

Bergink, et al. (1981) "*Effect of Oestriol, Oestradiol Valerate and Ethinyloestradiol on Serum Proteins in Oestrogen-Deficient Women*," Maturitas, 3 (3-4) : 241-247.

Bernard a. M. et al., (1994), *Menopausal: Bone and Therapeutic Regimens (Cont)*. International Journal of Gynecology & Obstetrics, pp. 124.

Botella et al. "*Regulation of Rat Uterine Steroid Receptors by Nomegestrol Acetate, A New 19-Nor-Progesterone Derivative*" Abstract of J. Pharmacol. Exp. Ther. Feb. 1989, 248(2): 758-61.

Botella et al. "*Kinetic Analysis of the Binding of Nomegestrol Acetate to the Progesterone Receptors in Rat Uterus by Competition Studies*" Fundam. Clin. Pharmacol. 1990; 4(5): 511-23.

Botella et al. "*Lack of Estrogenic Potential of Progesterone- or 17-Norprogesterone-Derived Progestins As Opposed to Testosterone or 19-Nortestosterone Derivatives On Endometrial Ishikawa Cells*" J. Steroid. Biochem. Mol. Biol. Oct. 1995, 55(1): 77-84.

Cohen et al. "*Traitement Des Femmes En Périménopause Par 5 Mg/J D'acétate De Nomégestrol, 20 Jours Par Cycle*" Contracept. Fertil. Sex. (1992)—vol. 20, No. 11, 1054-1057, including an English language abstract.

Conrad et al. "*Cardiovascular Risk Factors and Combined Estrogen-Progestin Replacement Therapu: A Placebo-Controlled Study With Noegestrol Acetate and Estradiol*", Fertility and Sterility, vol. 64, No. 5, 1995, pp. 957-962.

Couzinet et al. "*The Antigonadotropic Activity of Progestins (19-Norprogesterone And 19-Norprogesterone Derivatives) Is Not Mediated Through The Androgen Receptor*" J. Clin. Endocrinol. Metab. Dec. 1996; 4218-4223.

Couzinet B., et al. (1999) "*The Antigonadotropic Activity of A 19-Nor-Progesterone Derivative Is Exerted Both At the Hypothalamic and Pituitary Levels in Women*," The Journal of Clinical Endocrinology & Metabolism, vol. 84, No. 11, pp. 4191-4196.

Desreux et al. "*Effects of a Progestogen on Normal Human Breast Epithelial Apoptosis on Vitro and In Vivo*" The Breast (2003), 12, 142-149.

Dorangeon et al. "*Effects of Nomegestrol Acetate on Carbohydrate Metabolism*" Diabete & Metabolisme (paris) (1993), 19, 441-445.

Dorangeon et al. "*Short Term Effects on Lipids and Lipoproteins of Two Progestogens Used in Postmenopausal Replacement Therapy*" European Journal of Clinical Research (1992), 3: 187-193.

Dorangeon et al. "*Traitement De L'endométriose Par L'acétate De Nomégestrol*" Gynécologie, 1993, 1, 3, 139-143, including an English language abstract.

Duc et al. "*Interaction of [3H] Nomegestrol Acetate With Cytosolic Progesterone Receptors From The Rat Uterus*" Steroids, Jun. 1991, 56(6): 325-328.

at al. "*Antiandrogenic Properties of Nomegestrol Acetate*" Arzneim. Forsch. Drug/Res. 1995, 45(1): 70-74.

Foidart et al. "*Impact of Percutaneous Oestradiol Gels in Postmenopausal Hormone Replacement Therapy on Clinical Symtoms and Endometrium*" British Journal of Obstetrics and Gynaecology Mar. 1997, vol. 104, 305-310.

Lindberg et al. (1989) "*A Comparison Between Effects of Estradiol Valerate and Low Dose Ethinyl Estradiol on Haemostasis Parameters*" Thrombosis & Haemostasis, 61(1), pp. 65-69.

Nguyen -Pascal et al. "*Nomegestrol Acetate May Enhance The Skeletal Effects of Estradiol on Biochemical Markers of Bone Turnover in Menopausal Women After 12-Week Treatment Period*" Climacteric 2005; 8: 136-145.

Paris, et al. (1983), "*The Pharmacological Profile of TX 066 (17alpha-acetoxy-6-methyl-19-nor-4, 6-pregnadiene-3, 20-dione), a New Oral Progestative*". Arzneimittelforschung, vol. 33, No. 5, pp. 710-715.

Paris, et al. (1987) "*Extinction of Mineralocorticoid Effects in 19-Norprogesterone Derivatives: Structure-Activity Relationships,*" The Journal of Pharmacology and Experimental Therapeutics, vol. 243, No. 1, pp. 288-291.

Powers et al., "*Pharmacokinetics and Pharmacodynamics of Transdermal Dosage Forms of 17beta-estradiol: Comparison With Conventional Oral Estrogens Used for Hormone Replacement*", Am. J. Obstet. Gynecol. (1985), vol. 152, No. 8, pp. 1099-1106.

Reyonlds, J. "*MARTINDALE, The Extra Pharmacopoeia—Sex Hormone*" 30th Edition Pharmaceutical Press (1993), pp. 1166-1198. Suplemento afna No. 1, Mayo 1991, Seccion II 57.

Thomas J. L., et al. "*Les Progestatifs—Effets Biologiques Et Implications Theérapeutiques*" revue Française d'Endocrinologie, Nutition et Métabolisme, (1986), 27, No. 4-5, 389-403, including an English translation.

Timmer et al. "*Bioequivalence Assessment of Three Different Estradiol Formulations in Postmenopausal Women in an Open, Randomized, Single-Dose, 3-Way Cross-Over Study*" Europ.J.Drug. Metab.& Pharmaco., 1999, vol. 24, No. 1, pp. 47-53.

Von Schoultz, et al. (1989) "Estrogen Therapy and Liver Function-Metabolic Effects of Oral and Parenteral Administration," Prostate, 14 (4), pp. 389-395.

Williams et al., (Nov. 1998). "*Coadministration of Nomegestrol Acetate Does Not Diminish The Beneficial Effects of Estradiol On Coronary Artery Dilator Responses In Nonhuman Primates (Macaca fascicularis)*" Am. J. Obstet. Gynecol. vol. 179(5), pp. 1288-1294.

Zartarian et al. (1998) "*Effets Sur La Qualités Des Cycles Et Les Bouffées De Chaleur Du Nomégestrol Acétate Administré Seul Ou Associé En Séquentiel Inversé Au 17 Bêta Estradiol Cutané Chez Des Femmes En Périménopause*" Contracept. Fertil. Sex. vol. 26 (1), pp. 69-76, including an English language abstract.

Zartarian et al. (1998) "*Tolérance Biologique Et Clinique Du Nomégestrol Acétate, Administré Seul Puis Asocié En Séquentiel Inversé Au 17 Bêta Estradiol Cutané, Ches Des Femmes À Risques Présentant Une Dyslipoprotéinémie De Type IIa*" Annales d'endicrionologie (Paris), 59, 411-416, including and English language abstract.

Barret-Connor et al., (1989) "*Estrogen Replacement and Corony Heart Disease*" Cardiovascular clin., vol. 19, No. 3, pp. 159-172.

Zimmerman et al., (1999) "*Pharmacokinetics of Dienogest As A Single Drug or in Combination With Estradiol Valerate or Ethinylestradiol*," Drugs of Today, 35, pp. 27-39.

\* cited by examiner

HORMONAL COMPOSITION BASED ON A PROGESTATIONAL AGENT AND AN OESTROGEN AND USE THEREOF

SUMMARY OF THE TECHNICAL CONTENT OF THE INVENTION

The present invention relates to the field of therapeutic chemistry and more particularly to the field of pharmaceutical hormonal technique.

More precisely, its subjects are new pharmaceutical hormonal compositions formed of an estrogen-progestative association consisting of an estrogen compound and a progestative compound, in combination or admixed with one or more non-toxic, inert pharmaceutically-acceptable diluents suitable for oral administration.

The present invention also concerns the use of the estrogen-progestative mixture in which the estrogen compound and the progestative compound are administered in combination. The combined association may be prescribed continuously or discontinuously, with a view to produce a composition designed to treat estrogen deficiencies and to prevent osteoporosis and cardiovascular disorders in menopausal women.

A further object of the invention is a process for the preparation of the said new pharmaceutical estrogen-progestative compositions.

The present invention relates to the field of therapeutic chemistry and more particularly to the field of pharmaceutical hormonal technique.

More precisely, its subjects are new pharmaceutical compositions formed of an estrogen-progestative association designed to correct estrogen deficiencies in women, regardless of their origin, and more particularly in menopausal women.

In particular its objective is an estrogen-progestative association characterised in that it consists of dose units containing a combination of a progestative and an estrogen, both compounds being present at the same time in each medicinal dose.

Specifically, its subjects are new pharmaceutical compositions intended for hormone replacement therapy in menopause, which contain as active ingredient a progestational agent chosen from among nomegestrol and its esters and an estrogen agent chosen from among estradiol and its esters and the conjugated equine estrogens.

This association is intended for administration via the oral route, be it continuously or discontinuously.

As is known, over the course of less than a century the life expectancy of women has increased from 50 to 80 years, while the mean age at which the menopause begins has remained unchanged. Thus, women spend almost one-third of their life in a condition of estrogen deficiency, and this results in a higher risk of osteoporosis and cardiovascular disorders. Replacement therapy for the menopause has therefore become very widespread. It is administered either orally or, at least as regards its estrogen component, via the percutaneous route. Nevertheless, compliance seems better when the treatment is administered orally (ETTINGER et al., 1998).

Consecutive replacement therapy in the menopause cures the symptomatology of the climacteric.

It prevents osteoporosis and the onset of cardiovascular disorders. It creates artificial cycles which are followed by deprivational bleeding. This therapeutic scheme is particularly well suited to women whose menopause is recent, but it is not always well accepted in the long term, which partly explains the poor compliance with the treatment (DRAPIER FAURE E., Gynecology, 1992, 43: 271-280).

To overcome this drawback combined associations have been developed in which the two components are taken simultaneously, whether continuously or discontinuously, the effect of the progestative being to permanently oppose the proliferative action of the estrogen upon the endometrium, so inducing an atrophy of the endometrium and consequently preventing deprivation bleeding (HARGROVE J. T., MAXSON W. S., WENTZ A. C., BURNETT L. S., Obstet. Gynecol., 1989, 73: 606-612). In fact, under these conditions the endometrial atrophy is pronounced (WOLFE and PLUNKETT, 1994; PIEGSA et al., 1997; AFFINITO et al., 1998), there is no endometrial hyperplasia (STADBERG et al., 1996) and the frequency of bleeding is low and decreases with time (PIESGA et al., 1997; CARRANZA-LIRA, 1998; ETTINGER et al., 1998). With this type of treatment, compliance is generally good (EIKEN and KULTHOFF, 1995; DOREN et al., 1996), and certainly better than with consecutive treatment (EIKEN et al., 1996). The quality of life too seems improved (ULRICH et al., 1997). It is also known that this type of treatment protects the bone mass (EIKEN et al., 1996; EIKEN et al., 1997; HART et al., 1998; RECKER et al., 1999).

This "no-periods" scheme is particularly well suited for women whose menopause occurred already some time ago. Consecutive associations can be prescribed subsequently in order to improve long-term compliance with hormone replacement therapy in the menopause.

During sequential treatments the progestative dose chosen is that which, in the long term, leads to at least 1% of endometrial hyperplasia when the progestative is administered discontinuously for more than 10 days per cycle in menopausal women undergoing estrogen replacement therapy (WHITEHEAD et al., J. Reprod. Med., 1982, 27: 539-548; PATERSON et al., Br. Med. J., 1980, 22 Mar.: 822-824).

The progestative dose to be used in a combined replacement therapy is generally lower than that normally prescribed in consecutive schemes. Examples are micronised progesterone, dydrogesterone (FOX H., BAAK J., VAN DE WEIJER P., AL-AZZAWI E., PATERSON M., JOHNSON A., MICHELL G., BARLOW D., FRANCIS R., 7th International Congress on the Menopause, Stockholm, 20-24 Jun. 1993, abstr. 119) and medroxyprogesterone acetate (BOCANERA R., BEN J., COFONE M., GUINLE I., MAILAND D., SOSA M., POUDES G., ROBERTI A., BISO T., EZPELETA D., PUCHE R., TOZZINI R., 7th International Congress on the Menopause, Stockholm, 20-24 Jun. 1993, abstr. 40), which have been used respectively at doses of 100, 10 and 5 mg/day with encouraging results at the clinical and endometrial level.

Combined treatment is most often used continuously i.e. without interruption. Some, however, prefer to use it intermittently, for example on 25 days each month (BIRKAUSER M., et al.; Hormone substitution: a well defined indication and individual treatment schemes are decisive for the success of the therapy, Med. & Hyg., 1995, 53: 1770-1773). The purpose of interrupting the treatment is to remove the inhibition by the progestative of the synthesis of estradiol and progesterone receptors and so to avoid reducing the receptivity of the hormone-dependent tissues.

The progestative used according to the present invention is nomegestrol or one of its esters, mainly nomegestrol acetate. Nomegestrol acetate is a powerful progestative which is active via the oral route and has an original pharmacological profile:

in contrast to the derivatives of 19-nortestosterone, nomegestrol acetate shows no residual androgenic and estrogenic action;

in common with the derivatives of 17-alpha-hydroxyprogesterone it has a pure pharmacological profile, but in contrast to them it has a powerful antigonadotropic action.

It belongs to the category of qualified hybrid progestatives (OETTEL et al., 1999), which have no harmful metabolic effects because of the absence of a 17-alpha-ethinyl function, and which combine the advantages of the progesterone derivatives with those of the most modern among the 19-nortestosterone derivatives.

Its use in consecutive administration during the menopause at a dose of 5 mg/day for 12 days per cycle, in association with various types of estrogens, makes it possible to prevent endometrial hyperplasia as has been shown by a multicentric trial in 150 women over 1 year (THOMAS J. L., BERNARD A. M., DENIS C., 7th International Congress on the Menopause, Stockholm, 20-24 Jun. 1993, abstr. 372).

The absence of hyperplasia was confirmed in a study in which nomegestrol acetate was administered at the same dose for 14 days per cycle to women being treated with percutaneous estradiol (BERNARD A. M. et al., Comparative evaluation of two percutaneous estradiol gels in combination with nomegestrol acetate in hormone replacement therapy. XIV World Congress of Gynecology and Obstetrics, FIGO, Montreal, 24-30 Sep. 1994). This utilisation, which is covered by French Patent No. 2.737.411 in the name of the Applicant Company, claims a dose range from 1.5 to 6 mg and preferably from 2.5 to 5 mg.

The estrogen used is estradiol, free or esterified, and in particular estradiol valerate, or the conjugated equine estrogens, presented in a formulation that is active via the oral route. It has been shown that an estradiol dose of between 1 and 2 mg/day is enough to combat the estrogen deficiency in menopausal women.

The nomegestrol acetate and free or esterified estradiol, or the conjugated equine estrogens are administered in one of the forms that is suitable for oral administration: gelatine capsules, capsules, pills, powder sachets, tablets, coated tablets, sweetened tablets, etc.

The present invention is characterised by the fact that it is a new estrogen-progestative association which is active via the oral route, and is administered in combination. A further object of this invention is the use of compositions according to the invention to correct estrogen deficiencies and to prevent osteoporosis and cardiovascular disorders in menopausal women.

The present invention is also defined by:

a) The Fact that the Estrogen-Progestative Association Concerned is Different from Those Described Before Now for the Same Type of Indications.

Certain patents claim the continuous use of estrogen-progestative combinations for replacement therapy in menopause. Examples are U.S. Pat. No. 5,108,995 or EP 309263. It is evident, however, that these patents claim multisequential treatments with dose changes of the active ingredients. This is also true of the patents filed in the USA (U.S. Pat. No. 4,820,831 A) and in Europe (EP 136 011) in the name of PLUNKETT. Those patents claim the use of numerous estrogens and numerous progestatives in menopause replacement therapy. It seems, however, that the said claims do not cover the use of all progestatives, on the one hand for scientific reasons and on the other hand for scientific and legal reasons related to the wording of the claims of the two said patents:

1) The use of numerous progestatives is based on equivalences with one of them, in this case levonorgestrel. This approach seems unacceptable because different progestatives have very different pharmacological profiles and the doses to be used cannot be deduced from a simple and unique equivalence system, as becomes clear from the active dose ranges proposed for different progestatives in 3 different patents (Table 1).

It can be seen that the lower limit for the various progestatives varies in a ratio of 2.4 to 50 while the maximum dose varies in a ratio of 1 to 50. Thus, for indications of the same type, the dose range varies very considerably from one patent to the next and this shows that the system of equivalence does not lend credibility to the relationship which could be established between progestatives.

2) Apart from the above, it would be reasonable to think that the doses claimed should be based on data from clinical pharmacology and/or clinical data previously published and commonly accepted. Now, if the doses defined as in the PLUNKETT patents are considered, it is easy to see that in most cases the active doses published already a long time ago, i.e. before the said patents were filed (NEUMANN, 1977) or more recently (KUHL, 1996), are very coherent but only rarely lie within the dose ranges claimed in the patents in the name of PLUNKETT (Table 2).

This finding is also valid if, instead of the active doses as above, account is taken of the active dose ratios given by taking norgestrel as reference (=1) (Table 3).

TABLE NO. 1

Doses (µg/day) of the various progestatives claimed according to the patents

| PROGESTATIVE | PATENT | DOSE (µg/day) | |
| --- | --- | --- | --- |
| | | Minimum | Maximum |
| Levonorgestrel | WO 95/17194 | 60 | 125 |
| Levonorgestrel | EP 025607 Al | 25 | 100 |
| Levonorgestrel | PLUNKETT | 25 | 75 |
| Gestodene | WO 95/17194 | 50 | 75 |
| Gestodene | EP 025607 Al | 10 | 70 |
| Desogestrel | WO 95/17194 | 60 | 150 |
| Desogestrel | EP 025607 Al | 25 | 100 |
| 3-ketodesogestrel | WO 95/17194 | 60 | 150 |
| 3-ketodesogestrel | EP 025607 Al | 25 | 100 |
| Norethisterone | WP 95/17194 | 350 | 750 |
| Norethisterone | EP 025607 Al | 85 | 350 |
| Norethisterone | PLUNKETT | 150 | 1 000 |
| Norethisterone acetate | PLUNKETT | 100 | 1 000 |
| Norgestimate | WO 95/17194 | 200 | 300 |
| Norgestrel | PLUNKETT | 50 | 150 |
| Ethynodiol diacetate | PLUNKETT | 100 | 1 000 |
| Dihydrogesterone | PLUNKETT | 5 000 | 30 000 |
| MPA | PLUNKETT | 1 000 | 15 000 |
| Norethynodrel | PLUNKETT | 200 | 5 000 |
| Allylestrenol | PLUNKETT | 1 000 | 10 000 |
| Lynoestrenol | PLUNKETT | 100 | 2 000 |
| Quingestanol acetate | PLUNKETT | 50 | 1 000 |
| Medrogestone | PLUNKETT | 1 000 | 10 000 |
| Norgestrienone | PLUNKETT | 20 | 200 |
| Dimethisterone | PLUNKETT | 500 | 15 000 |
| Ethisterone | PLUNKETT | 1 000 | 25 000 |
| Cyproterone acetate | PLUNKETT | 100 | 10 000 |
| Cyproterone acetate | WO 95/17194 | 100 | 200 |

TABLE NO. 2

Doses of each progestative according to the various bibliographical references

| | U.S. Pat. No. 4,826,831 | | NEUMANN PUBLICATION | | | | KUHL | |
|---|---|---|---|---|---|---|---|---|
| | | | Endometrium | Menstruation | Ovulation | Contraception | Endometrium | Ovulation |
| | Min. | Max. | (1) | (2) | (3) | (4) | (1) | (3) |
| Levonorgestrel | 25 | 75 | | | | | 400 | 60 |
| Norgestrel | 50 | 150 | 1200 | 2000 | 100 | 250 | | |
| Norethisterone | 150 | 1000 | 12500 | 5000 | 800 | 1000 | 10000 | 400 |
| Norethisterone acetate | 100 | 1000 | 4500 | | 800 | 1000 | | |
| Ethynodiol diacetate | 100 | 1000 | | | | | | |
| Dydrogesterone | 5000 | 30000 | | | | | | |
| MPA | 1000 | 15000 | 5500 | 25000 | | 5000 | | |
| Norethynodrel | 200 | 5000 | 10000 | 7500 | 6000 | 2500 | | |
| Allylestrenol | 1000 | 10000 | 1750 | | | | | |
| Lynoestrenol | 100 | 2000 | 5000 | | | 2500 | | |
| Quingestanol acetate | 50 | 1000 | | | | | | |
| Medrogestone | 1000 | 10000 | | | | | | |
| Norgestrienone | 20 | 200 | | | | | | |
| Dimethisterone | 500 | 15000 | | | | | | |
| Ethisterone | 1000 | 25000 | | | | | | |
| CIP acetate | 100 | 10000 | 1000 | | 1000 | 2000 | 2000 | 1000 |

The cases appearing in bold above correspond to active doses outside the dose ranges claimed in the "PLUNKETT" patents. The doses (μg/day) are those necessary to induce transformation of the endometrium (1), to produce an adequate delay in the onset of periods (2), to inhibit ovulation (3), or to have a contraceptive effect (4).

TABLE NO. 3

Dose ratios of each progestative according to the various bibliographical references
The reference progestative is norgestrel (=1)

| | U.S. Pat. No. 4,826,831 | | NEUMANN Ratios | | | |
|---|---|---|---|---|---|---|
| | Ratios | | Endometrium | Ovulation | Menstruation | Contraception |
| | Min. | Max. | (1) | (3) | (2) | (4) |
| Levonorgestrel | 0.5 | 0.5 | | | | |
| Norgestrel | 1.0 | 1.0 | 1.0 | 1.0 | 1.0 | 1.0 |
| Norethisterone | 3.0 | 6.7 | *10.4* | *8.0* | *2.5* | 4.0 |
| Norethisterone acetate | 2.0 | 6.7 | 3.8 | *8.0* | | 4.0 |
| Ethynodiol diacetate | 2.0 | 6.7 | | | | |
| Dydrogesterone | 100.0 | 200.0 | | | | |
| MPA | 20.0 | 100.0 | 4.6 | | *12.5* | 20.0 |
| Norethynodrel | 4.0 | 33.3 | 8.3 | *60.0* | *3.8* | 10.0 |
| Allylestrenol | 20.0 | 66.7 | *1.5* | | | |
| Lynoestrenol | 2.0 | 13.3 | 4.2 | | | 10.0 |
| Quingestanol acetate | 1.0 | 6.7 | | | | |
| Medrogestone | 20.0 | 66.7 | | | | |
| Norgestrienone | 0.4 | 1.3 | | | | |
| Dimethisterone | 10.0 | 100.0 | | | | |
| Ethisterone | 20.0 | 166.7 | | | | |
| CIP acetate | 2.0 | 66.7 | *0.8* | 10.0 | | 8.0 |

The cases appearing in bold and Italics correspond to active doses outside the ratio ranges claimed in the U.S. and EP patents cited in the name of PLUNKETT. For the meanings of (1), (2), (3) and (4), see Table 2.

Reasoning Related to the Claims

1) In the US patent cited above, Claims 1 and 2 relate to continuous treatments; the only progestatives claimed are dl-norgestrel and levonorgestrel. The subsequent claims concern discontinuous multisequential treatment, i.e. a therapeutic scheme different from that proposed in the present patent application. For this latter type of therapeutic regime the number of progestatives claimed is larger but the list thereof is precise and limited, as emerges from the Markush-type presentation of the said claims, and it does not include nomegestrol and its esters.

2) The European patent only claims the continuous combined treatment; the estrogens and progestatives claimed are listed in tables present in the body of the text and summarised in the claims. There too, nomegestrol and its esters do not feature in the lists of progestatives that can be used. Now, nomegestrol acetate is characterised by a powerful progestational action, an absence of residual androgenic and estrogenic effects, and a powerful anti-estrogenic action which is manifested at the level of the endometrium by marked anti-mitotic activity and, consequently, a pronounced atrophying effect. Accordingly, it cannot be likened to the other progestatives and to think in terms of a dose correspondence relative to another progestative taken as reference cannot but be erroneous. Moreover, nomegestrol acetate is characterised by excellent tolerance; it has no effect on the lipids profile, the tolerance to glucides, the arterial pressure and the coagulation factors, even when used at doses higher than those described in the present patent application and in prolonged treatments (BASDEVANT et al., 1997). This aspect is very important because all therapists in common strive to use the treatment with least possible toxicity involving the lowest possible doses. In this respect, nomegestrol acetate differs from many derivatives of 19-norteststerone cited in the PLUNKETT patents, which are progestatives characterised by androgenic and estrogenic effects which can have consequences at the level of the endometrium and which also have harmful metabolic effects.

For the same reasons as those mentioned above, none of the numerous publications that deal with the continuous combined treatment of the menopause can have a bearing on the present invention because none of these publications deals with an association of nomegestrol acetate with an estrogen. This for example applies to associations of estradiol and norethisterone acetate (STADBERG et al., 1996; DOREN and SCHNEIDER, 1996; DOREN et al., 1997; EIKEN et al., 1997; PIEGSA et al., 1997; HART et al., 1998), estradiol and medrogestone (AFFINITO et al., 1998), estradiol and norgestrel (WOLFE and PLUNKETT, 1994), estradiol valerianate and chlormadinone acetate (RAUCH and TAUBERT, 1993), and conjugated equine estrogens with medroxyprogesterone acetate (REUBINOFF et al., 1995; WOLFE and HUFF, 1995; MIZUNUMA et al., 1997) or medrogestone (RECKER et al., 1999).

b) The Fact that this Estrogen-Progestative Association is Different from the Association Previously Patented by the Applicant.

In effect, French Patent No. 2.754.179 in the name of the Applicant claimed an association of estradiol and nomegestrol acetate for the combined replacement therapy of the menopause. The dose range claimed on the basis of previous experience with nomegestrol acetate in consecutive therapy was from 1.5 to 3.75 mg, preferably 2.5 mg. Now, clinical trials on a broader scale have shown that in an unexpected way, very much lower doses of nomegestrol acetate can induce endometrial atrophy with very good control of bleeding. This observation is important because it allows the nomegestrol acetate doses to be reduced still further, so that it can be used with still greater safety. The doses of Estradiol claimed in this patent ranged from 0.5 to 3 mg. The same doses of Estradiol are used but the ratio estrogen/progestative appears to be markedly altered 1:5 instead of 6:1.

c) Appropriate Production Method for the Pharmaceutical Forms

The invention concerns a production method with which the two active ingredients can be combined in one and the same pharmaceutical form.

The compositions according to the invention, based on nomegestrol acetate and free or esterified estradiol or conjugated equine estrogens, are administered either continuously or intermittently (from 21 to 28 days per month).

According to a particular embodiment of the invention, the compositions contain a quantity of nomegestrol acetate ranging from 0.3 to 1.5 mg and a quantity of free or esterified estradiol or conjugated equine estrogens ranging from 0.3 to 3 mg. Preferably, the optimum formulations contain 0.625 to 1.25 mg of nomegestrol acetate associated with 0.5 to 1.5 mg of free estradiol or 1.5 to 2 mg of estradiol ester or 0.312 to 0.625 mg of conjugated equine estrogens, in each daily dose.

This mode of combined administration is indicated in menopausal women, whether the menopause is natural or the result of surgery; the estrogen-progestative combination is intended to compensate the functional disturbances induced by the menopausal estrogen deficiency, while maintaining endometrial atrophy and avoiding the appearance of deprivation bleeding in most of the women.

A further objective of the present invention is a process for obtaining new pharmaceutical compositions, which consists in mixing the active ingredients: nomegestrol acetate and free or esterified estradiol or conjugated equine estrogens, with one or more inert, non-toxic and pharmaceutically acceptable diluents or vehicles.

Among the excipients may be mentioned binding and dissolution-promoting agents, compaction agents, disintegration agents and slip-promoting agents.

The said mixture is compacted directly or in several stages to form tablets which can be protected on the surface, if desired, with a film, a coating, or by being made into dragees. The production of tablets by direct compaction makes possible the maximum reduction of the proportion of dilution agents, binding agents, disintegration agents and slip-promoting agents.

Soft gelatine capsules can be produced by mixing the active ingredients with an inert diluent and with a sliding agent.

The tablets contain, in particular, agents which dilute the mass such as lactose, sorbitol for direct compaction, as marketed under the name NEOSORB 60, Palatinite which is the registered trademark designating an equimolar mixture of isomer of [D]glucopyranosido-1,6-mannitol and [D]glucopyranosido-1,6-glucitol crystallised with two water molecules, mannitol, sorbitol, or the lactose/PVP mixture marketed under the name Ludipress.

The compaction binding agents are generally microcrystalline celluloses such as those marketed under the name AVICEL PH 101 or AVICEL PH 102. Polyvinylpyrrolidone also plays an important part by facilitating the agglomeration of the powders and the compressibility of the mass. The polyvinylpyrrolidones used for this purpose have molecular weights between 10 000 and 30 000, such as Povidone, or Kollidon graded from 12 to 30.

The mixture also contains slip-gliding or anti-electrostatic agents which prevent the powder from agglomerating in the feed hoppers. In this connection the colloidal silicas marketed under the name AEROSIL, 100 or AEROSIL 200 may be mentioned.

The mixture also contains disintegration agents which make for disintegration or crumbling in accordance with pharmaceutical standards. As useful disintegration agents it may be mentioned the cross-linked vinylpyrrolidone polymers such as those marketed under the names Polyplasdone or Polyclar AT, carboxymethyl starches such as those marketed under the names Amijel or Explotab, or cross-linked carboxymethyl celluloses such as the compound sold under the name AC-DI-SOL.

In addition, the preparation contains lubricant agents which facilitate compaction and the ejection of the tablet from the tableting machines. As lubricants it may be mentioned glycerol palmitostearate as sold under the name Precirol, magnesium stearate, stearic acid or talc.

After compaction the tablets can be coated to improve their storage properties or to facilitate swallowing.

The coating agents are either cellulosic, such as cellulose phthalate (Sepifilm, Pharmacoat), or polyvinylic of the OPADRY PVA or Sepifilm ECL type, or saccharosic such as the sugar for coating of the Sepisperse DR, AS, AP or K types (coloured).

The tablets, whether coated or not, can in addition be coloured at the surface or throughout, with mineral, vegetable or synthetic dyes (for example lacquer with quinoline-yellow, of E 104 or iron oxides).

The proportions of the various constituents vary according to the nature of the tablet to be made.

The content of active ingredients can range from 0.3 to 1.5 mg for the nomegestrol acetate and from 0.3 to 3 mg for the free or esterified estradiol or for the conjugated equine estrogens. The dilution agents range from 20 to 75% of the total mass, the gliding agents from 0.1 to 2% of the total mass, the compaction binding agents range from 2 to 20%, the polyvinylpyrrolidone from 0.5 to 15%, the disintegration agents range from 2 to 5.5% for cross-linked polyvinylpyrrolidone or carboxymethyl starch, and from 2.0 to 3.0% for croscarmellose.

The quantities of lubrication agents vary from 0.1 to 3.0%, depending on the type of agent.

The compositions according to the invention are intended to be administered once per day. However, depending on the therapeutic needs, the administration may be divided (twice daily) or, on the contrary repeated (two tablets per day).

The following examples illustrate the invention without limiting it in any way.

EXAMPLE 1

Examples of Formulations

The association of nomegestrol acetate and estradiol is presented in the form of plain or film-coated tablets.

The mixture of ingredients can either be compacted directly, or a preliminary estradiol mixture can be made into which the nomegestrol acetate and the other excipients are then incorporated in dry form. The preliminary estradiol mixture is made by dissolving the estradiol in an alcoholic solution of microcrystalline cellulose, PVP and lactose, drying it, and then grinding and calibrating it. This process is advantageous because tablets made from a preliminary estradiol mix have an estradiol dissolution profile which is appreciably better compared with tablets made by direct compaction.

The final mixture can contain from 1.5 to 5% of estradiol in povidone (5 to 25%), microcrystalline cellulose (5 to 15%) and lactose (enough to make up to 100%). It can be advantageous to introduce an anti-oxidant agent such as alpha-tocopherol or ascorbic acid during the preparation of the preliminary mix.

As an example, the following preliminary mix can be mentioned:

| FORMULATIONS | in mg/one tablet | in % |
| --- | --- | --- |
| Estradiol | 1.50 | 1.82 |
| PVP K25 | 13.50 | 16.36 |
| Lactose 8195 | 60.00 | 72.73 |
| Microcrystalline cellulose | 7.50 | 9.09 |
| TOTAL DRY MIX | 82.50 | 100.00 |

This preliminary mix is introduced into the final mixture to obtain a tablet by direct compaction.

The finished tablets, uncoated, generally weigh 60 to 200 mg and have the following overall formulation:

| FORMULATIONS OF THE UNCOATED TABLETS | |
| --- | --- |
| Composition | in mg per tablet |
| Estradiol (pre-mix, quantity sufficient for) | 0.3 to 3.0 |
| Nomegestrol acetate | 0.300 to 1.500 |
| Colloidal silica | 0.400 to 2.000 |
| Crospovidone | 2.500 to 4.000 |
| Lactose | 60.000 to 80.000 |
| Cellulose | 10.000 to 25.000 |
| Stearic acid | 0.900 to 3.000 |
| Talc | 0.450 to 1.500 |

As examples, tablets can be mentioned which weigh 185 mg and have the following formulas:

Example of the formulation (UF = unitary formulation) of 185 mg tablets

| FORMULATION | UF mg per 1 tablet of 185 mg | UF % |
| --- | --- | --- |
| Estradiol | 1.500 | 0.811 |
| Nomegestrol acetate | 0.625 | 0.338 |
| Lactose | 131.790 | 71.238 |
| Cellulose (Avicel PH 101) | 27.810 | 15.032 |
| Povidone (K25) | 13.500 | 7.297 |
| Precirol (ATO5) | 2.780 | 1.503 |
| Colloidal silica (Aerosil 200) | 1.000 | 0.540 |
| Crospovidone (Polyplasdone XL) | 6.000 | 3.243 |
| TOTAL | 185.00 | 100.000 |

Example of the formulation (UF = unitary formulation) of 185 mg tablets

| FORMULATION | UF mg per 1 tablet of 185 mg | UF % |
| --- | --- | --- |
| Estradiol | 0.500 | 0.270 |
| Nomegestrol acetate | 0.625 | 0.339 |
| Lactose | 136.787 | 73.934 |
| Cellulose (Avicel PH 101) | 32.813 | 17.736 |
| Povidone (K25) | 4.500 | 2.432 |
| Precirol (AT05) | 2.775 | 1.500 |
| Colloidal silica (Aerosil 200) | 1.000 | 0.540 |
| Crospovidone (Polyplasdone XL) | 6.000 | 3.243 |
| TOTAL | 185.00 | 100.000 |

Example of the formulation (UF = unitary formulation) of 120 mg tablets

| FORMULATION | UF mg per 1 tablet of 120 mg | UF % |
| --- | --- | --- |
| Estradiol | 1.500 | 1.250 |
| Nomegestrol acetate | 1.250 | 1.042 |
| Lactose | 84.000 | 70.000 |
| Cellulose (Avicel PH 101) | 11.250 | 9.375 |
| Povidone (K25) | 13.500 | 11.250 |
| Colloidal silica (Aerosil 200) | 1.000 | 0.833 |
| Crospovidone (Polyplasdone XL) | 3.000 | 2.500 |
| Magnesium stearate | 1.000 | 0.833 |
| Talc | 1.000 | 0.833 |
| Stearic acid AC/50VG | 2.500 | 2.083 |
| TOTAL | 120.00 | 100.000 |

Example of the formulation (UF = unitary formulation) of 120 mg tablets

| FORMULATION | UF mg per 1 tablet of 120 mg | UF % |
|---|---|---|
| Estradiol | 0.500 | 0.417 |
| Nomegestrol acetate | 0.625 | 0.521 |
| Lactose | 89.000 | 74.167 |
| Cellulose (Avicel PH 101) | 16.875 | 14.062 |
| Povidone (K25) | 4.500 | 3.750 |
| Colloidal silica (Aerosil 200) | 1.000 | 0.833 |
| Crospovidone (Polyplasdone XL) | 3.000 | 2.500 |
| Magnesium stearate | 1.000 | 0.833 |
| Talc | 1.000 | 0.833 |
| Stearic acid AC/50VG | 2.500 | 2.083 |
| TOTAL | 120.00 | 100.000 |

Example of the formulation (UF = unitary formulation) of 80 mg tablets

| FORMULATION | UF mg per 1 tablet of 80 mg | UF % |
|---|---|---|
| Estradiol | 0.500 | 0.625 |
| Nomegestrol acetate | 0.625 | 0.781 |
| Kollidon 25 | 4.500 | 5.625 |
| Lactose M | 59.735 | 74.669 |
| Cellulose (Avicel PH 101) | 12.000 | 15.000 |
| Crospovidone (Polyplasdone XL) | 0.800 | 1.000 |
| Talc | 0.700 | 0.550 |
| Colloidal silica (Aerosil 200) | 0.440 | 0.550 |
| Magnesium stearate | 0.700 | 0.875 |
| TOTAL | 80.000 | 100.000 |

Example of the formulation (UF = unitary formulation) of 80 mg tablets

| FORMULATION | UF mg per 1 tablet of 80 mg | UF % |
|---|---|---|
| Estradiol | 1.000 | 1.250 |
| Nomegestrol acetate | 1.250 | 1.563 |
| Kollidon 25 | 9.000 | 11.250 |
| Lactose M | 54.110 | 67.637 |
| Cellulose (Avicel PH 101) | 12.000 | 15.000 |
| Crospovidone (Polyplasdone XL) | 0.800 | 1.000 |
| Talc | 0.700 | 0.875 |
| Colloidal silica (Aerosil 200) | 0.440 | 0.550 |
| Magnesium stearate | 0.700 | 0.875 |
| TOTAL | 80.000 | 100.000 |

These tablets may be coated, for example with:
film-forming agents based on polyvinyl alcohol of the type OPADRY PVA "moisture barrier" (polyvinyl alcohol, titanium dioxide, purified talc, lecithin, xanthan gum, pigments, lacquers), or film-forming agents based on cellulose of the type SEPIFILM L.P. ([H.P.M.C. (hydroxypropylmethylcellulose)], microcrystalline cellulose, stearic acid, pigments, lacquers).

EXAMPLE II

Dissociation of the Antimitotic and Differentiating Effects of Nomegestrol Acetate on Endometrial Cells Menopausal women, whether naturally or as the result of surgery, were subjected to a sequential estrogen-progestative therapy. From Day 1 to Day 12 they received 30 µg of ethinyl estradiol and then, from Day 13 to Day 22, the same dose of ethinyl estradiol associated with different doses of nomegestrol acetate or chlormadinone acetate. The doses were as follows:

| | | | | | | | |
|---|---|---|---|---|---|---|---|
| Nomegestrol acetate (mg): | 0.1 | 0.25 | 0.5 | 1 | | 2.5 | 5 and 10 |
| Chlormadinone acetate (mg): | 0.1 | | 0.5 | 1 | 2 | | 5 and 10 |

The number of women was between 2 and 11, depending on the group. There was then a therapeutic pause of 7 days followed by a second treatment cycle.

The parameters taken into account were as follows:
the interval before periods commenced after the therapy had been interrupted, following the first and second treatment cycles;
the histological appearance of the endometrium recovered in a biopsy carried out between Day 17 and Day 20 of the second cycle.

The results showed that:
The interval before periods appeared is a function of the dose and is similar for both products. The dose required for no periods to appear before the end of the therapy is between 0.2 and 0.3 mg/day for both products (Table 1).
The transformation of the endometrium into a secretory endometrium is total with both products from 1 mg/day upwards, but decreases at the highest doses (10 mg/day).
The proliferation activity, expressed as the number of mitoses in the glandular cells, seems more strongly inhibited by nomegestrol acetate than by chlormadinone acetate. Mitosis no longer takes place in women treated with a dose equal to or higher than 0.5 mg/day of nomegestrol acetate, while mitosis is still evident with a daily dose of 1 mg/day of chlormadinone acetate (Table 2).

It can therefore be concluded that at the endometrial level, nomegestrol acetate and chlormadinone acetate are not comparable: the secretory transformation activity is comparable but nomegestrol acetate is characterised by a very marked antimitotic and antiproliferative action.

TABLE 1

Interval before the appearance of periods (days) after the therapy is discontinued

| | Dose (mg/day) | | | | | | | |
|---|---|---|---|---|---|---|---|---|
| Progestative | 0.1 | 0.25 | 0.5 | 1.0 | 2.0 | 2.5 | 5 | 10 |
| Nomegestrol acetate | −0.5 ± 1.5 | −0.5 ± 0.5 | 1.5 ± 0.5 | 2.7 ± 0.2 | | 3.2 ± 0.2 | 4.3 ± 0.4 | 3.8 ± 0.8 |
| Chlormadinone acetate | −2.3 ± 0.5 | | 2.0 ± 0.6 | 3.8 ± 0.3 | 3.8 ± 0.3 | | 5.5 ± 1.5 | 5.5 ± 0.5 |

TABLE 2

Evaluation of the number of mitoses (% of section in which mitoses were present)

| | | Dose (mg/day) | | | | | | | |
|---|---|---|---|---|---|---|---|---|---|
| | | 0.1 | 0.25 | 0.5 | 1 | 2 | 2.5 | 5 | 10 |
| Glands | Nomegestrol acetate | 50 | 50 | 0 | 0 | 0 | 0 | 0 | 30 |
| | Chlormadinone acetate | 90 | | | 50 | 0 | | 0 | 0 |

EXAMPLE III

A trial was carried out to study the effects on the endometrium of the continuous combined association of an oral estradiol dose equivalent to 1.5 mg and various doses of nomegestrol acetate.

This consisted in the treatment for 6 consecutive months of 179 women who had been menopausal for at least 3 years, with 1.5 mg per day of estradiol combined continuously with 4 different doses of nomegestrol acetate: 5 mg/day (n=47); 2.5 mg/day (n=42); 1.25 mg/day (n=43) and 0.625 mg/day (n=47).

The impact of these four associations on the endometrium was evaluated by recording the characteristics of genital bleeding, measuring the thickness of the endometrium by endovaginal echography before and at the end of the therapy, and by carrying out a biopsy of the endometrium before and at the end of the therapy.

The percentages of women who showed no genital bleeding at all throughout the therapy were respectively 42.5-58.1-52.4 and 68.1%, with the doses of 0.625-1.25-2.5 and 5 mg of nomegestrol acetate per day. The percentages observed are not statistically different between the groups, but the relation between the dose and the incidence of bleeding is significant.

The tables attached indicate, for each nomegestrol acetate dose, the results of the echographic examination and biopsy of the endometrium carried out at the end of the 6 months of treatment.

At the end of the therapy, the mean thickness of the endometrium is not different between the groups. The increase of the endometrial thickness under therapy is 0.39 mm on average with the smallest nomegestrol acetate dose. This thickening increases slightly as a function of dose, becoming 1.56 mm in the group of women who received 5 mg/day of the progestative, but the relation between the variation of thickness and the dose variation does not reach the threshold of statistical significance.

The biopsies of the endometrium examined at the end of the trial showed no proliferative or hyperplasic appearance of the uterine mucosa. The highest percentage of secretory endometria was observed in the women who had received the highest progestative dose; it decreased progressively and in a statistically significant way with the dose. In contrast, the highest percentage of atrophic endometria was found at the lowest progestative dose and this decreased as the dose increased.

These results are unexpected in the sense that they show that low doses of nomegestrol acetate administered in continuous combination with an estrogen are capable of preventing the growth of the uterine mucosa and keeping it in an atrophic condition, whereas, in contrast to higher doses, they are insufficient to induce a secretory transformation of the endometrium.

Thus, this trial reveals a surprising decoupling of the anti-estrogenic effect of nomegestrol acetate from its progestational effect, when it is administered in continuous combination with estrogens.

The anti-estrogenic effect is preponderant since it is detectable when the progestative, administered continuously with an estrogen, is given at low doses. These doses are insufficient to bring about secretory transformations of the uterine mucosa. At higher doses and with the same therapeutic scheme, the secretory effect predominates, though without allowing excessive proliferation of the endometrium.

TABLE I

Endometrial thickness after 6 months of continuous treatment with several combined associations based on estradiol (2 mg of estradiol valerate) and nomegestrol acetate (NOMAC) at various doses

| Doses of NOMAC (mg/day) | 0.625 (n = 35) | 1.25 (n = 33) | 2.5 (n = 34) | 5 (n = 41) |
|---|---|---|---|---|
| Mean thickness at the end of the treatment (mm) | 3.18 (1.65) | 4.05 (3.75) | 3.93 (2.10) | 3.83 (2.72) |
| Mean thickness increase under the treatment (mm) | 0.39 (1.67) | 1.12 (3.67) | 1.36 (1.54) | 1.57 (2.39) |

( ) = standard deviation

TABLE 2

Histological appearance of the endometrium after 6 month of continuous treatment with several combined associations containing estradiol (2 mg of estradiol valerate) and nomegestrol acetate (NOMAC) at various doses

| Doses of NOMAC (mg/day) | 0.625 (n = 32) | 1.25 (n = 33) | 2.5 (n = 34) | 5 (n = 40) |
|---|---|---|---|---|
| Absence of endometrium | 5 (15.6) | 10 (30.3) | 3 (8.8) | 3 (7.5) |
| Atrophic endometrium | 19 (59.4) | 10 (30.3) | 8 (23.5) | 3 (7.5) |
| Secretory endometrium | 8 (25.0) | 12 (36.4) | 22 (64.7) | 34 (85.0) |
| Polyps | 0 | 1 (3.0) | 1 (2.9) | 0 |

( ) = percentage
In no case was the endometrium proliferative or hyperplasic.

The invention claimed is:

1. A hormonal replacement therapy method for treating an estrogen deficient, menopausal woman comprising orally administering daily without interruption to such menopausal woman a composition containing from 0.5 to 1.5 mg of free estradiol or 1.5 to 2 mg of an estradiol ester, and from 0.625 to 1.25 mg of nomegestrol acetate per daily dose so as to achieve hormonal replacement therapy while preventing growth of uterine mucosa, inducing endometrial atrophy, and keeping the uterine mucosa in an atrophic condition.

2. The method of claim 1, in which the composition contains 17β-estradiol.

3. The method of claim 1, in which the composition contains estradiol valerate.

4. The method of claim 1, in which the composition contains from 0.5 to 1.5 mg of free estradiol per daily dose.

5. The method of claim 1, in which the composition contains from 1.5 to 2 mg of estradiol ester per daily dose.

* * * * *